United States Patent [19]

Shell et al.

[11] Patent Number: 4,492,753

[45] Date of Patent: Jan. 8, 1985

[54] METHOD AND MEANS FOR ASSESSMENT AND PREDICTION OF RISK OF SUBSEQUENT ISCHEMIC CARDIAC EVENTS

[75] Inventors: William E. Shell, Los Angeles; Michael H. Burnam, Hidden Hills; Zoltan A. Tokes, Los Angeles, all of Calif.

[73] Assignee: Immudx, Inc., San Diego, Calif.

[21] Appl. No.: 433,153

[22] Filed: Oct. 6, 1982

[51] Int. Cl.³ .................. C12Q 1/50; G01N 33/68
[52] U.S. Cl. .................. 435/17; 128/637; 436/87; 436/183
[58] Field of Search ............ 436/2, 86, 87, 183, 436/63; 435/15, 17; 128/635, 637

[56] References Cited

U.S. PATENT DOCUMENTS

| 3,540,984 | 11/1970 | Deutsch | 435/15 |
| 3,806,422 | 4/1974 | Moyer et al. | 435/17 X |
| 3,891,507 | 6/1975 | Breuer | 435/15 X |
| 4,105,499 | 8/1978 | Kiyasu | 435/17 |
| 4,237,219 | 12/1980 | Roberts | 435/17 X |
| 4,387,160 | 6/1983 | Gomez et al. | 435/17 X |

FOREIGN PATENT DOCUMENTS 2089981  12/1980  United Kingdom .................. 435/17

OTHER PUBLICATIONS

Smith et al., Clin. Chim. Acta., vol. 81, (1977), pp. 75–85.
Shell et al., Am. J. of Cardiology, vol. 44, Jul. 1979, pp. 67–75.
Shell et al., J. of Clin. Investigation, vol. 50, (1971), pp. 2614–2625.
Lott et al., Clinical Chemistry, vol. 26, #9, (1980), pp. 1241–1250.
Galen et al., J.A.M.A., vol. 232, #2, 4/14/75, pp. 145–147.

Primary Examiner—Arnold Turk
Assistant Examiner—Robert J. Hill, Jr.
Attorney, Agent, or Firm—Fulwider, Patton, Rieber, Lee & Utecht

[57] ABSTRACT

A method and means for determining the risk of future cardiac ischemic events in a patient after a sentinel event in that same patient, wherein levels of acid glycoprotein and CK-MB are monitored relative to predetermined threshold levels, within a prescribed time frame after the sentinel event, and these monitored levels are then correlated with the predicted likelihood of future cardiac ischemic events to classify such cardiac patients into categories of risk.

16 Claims, 1 Drawing Figure

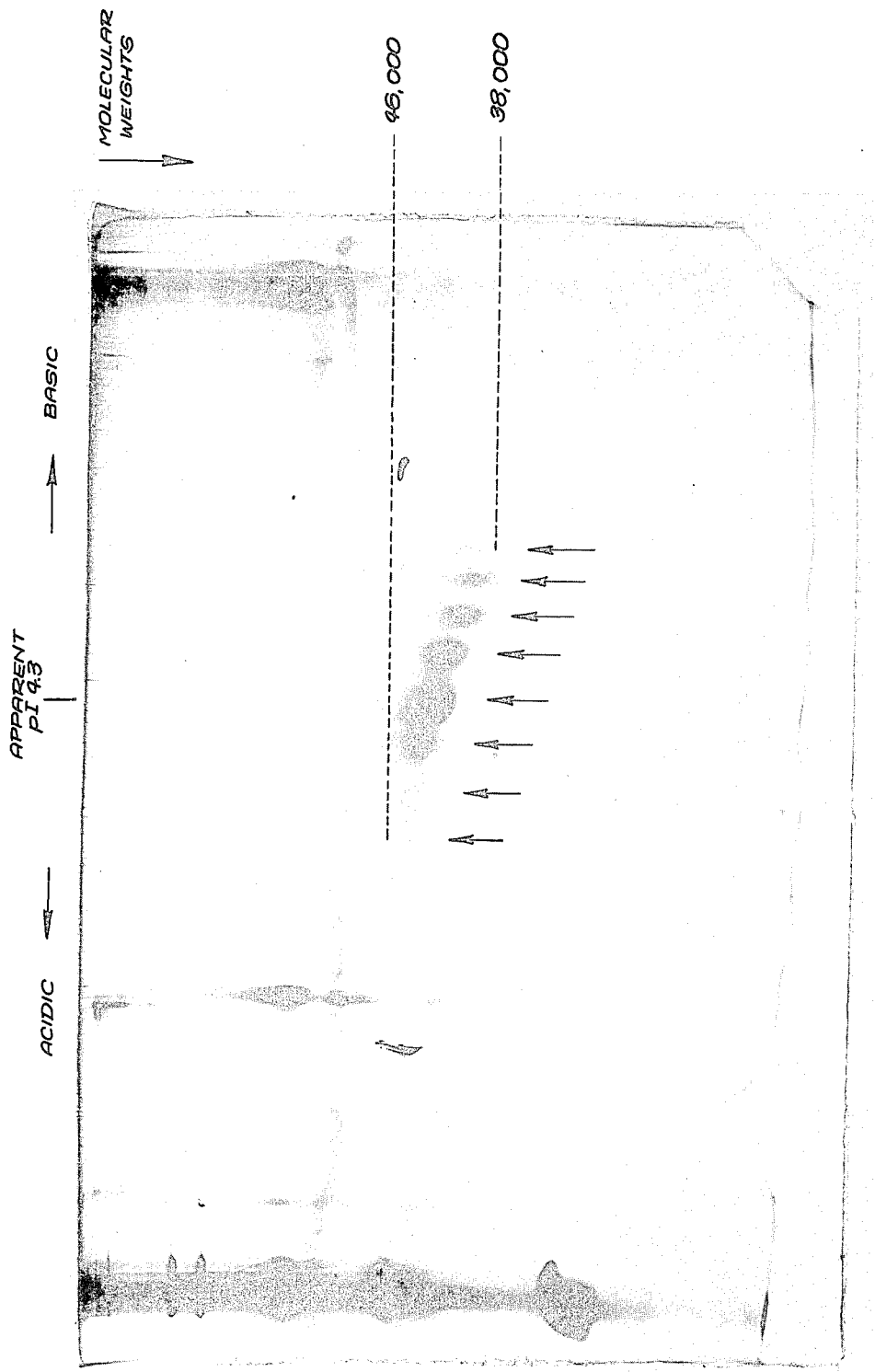

METHOD AND MEANS FOR ASSESSMENT AND PREDICTION OF RISK OF SUBSEQUENT ISCHEMIC CARDIAC EVENTS

BACKGROUND OF THE INVENTION

The present invention relates generally to the evaluation of cardiac patients in order to assess their risk for future ischemic heart events.

Presently, it is known that many proteins are associated with ischemic heart events. One of the earliest proteins to show a relationship with ischemic heart events is creatine kinase, hereinafter referred to as CK. Since 1962, blood tests for total CK enzyme activity have been used in the diagnosis and estimation of the severity of myocardial infarcts. Since the 1970's, it has been known that one particular isoenzyme form of CK, i.e. CK-MB, is released into the blood stream following a myocardial infarct. In addition, other proteins have been associated with myocardial infarction including serum glutamic oxylotransamenase (SGOT), lactic dehydrogenase (LDH), isocitric dehydrogenase, haptoglobin, alpha-l-acid glycoprotein, antitrypsin, C-reactive protein, and fibrinogen.

CK activity and CK-MB activity have also been related to the size of the infarct (Shell et al, Sensitivity and Specificity of MB-Creatine Kinase Activity Determined with Column Chromatography, Am. J. Cardiol., 44: 67, 1979, and Shell et al, Quantitative Assessment of the Extent of Myocardial Infarction in the Conscious Dog by Means of Analysis of Serial Changes in Serum Creatine Phosphokinase Activity, J. Clin. Invest. 50: 2614, 1971). It is generally accepted by those skilled in the art that patients admitted to rule out myocardial infarction experience a 10–12% one year mortality rate regardless of the results of total CK enzyme testing, with no ability to segregate patients with varying degrees of risk. According to Smith, et al., Clin Chim Acta 81: 75–85 (1977), a quantitative relationship with enzymatic infarct size also exists for alpha-l-acid glycoproteins.

While the aforedescribed proteins may be useful in determining whether an individual has suffered a recent myocardial infarction or in assisting physicians in ascertaining the size of that infarct, none of these proteins have been shown to have any significant predictive correlation to future ischemic events—future myocardial infarction, future unstable angina pectoris or future sudden cardiac-associated death. Prediction of the probability of future ischemic events is a major problem for individual patients since undue treatment could be avoided, if the patients could be identified who are at low risk. Alternatively, patients who would be amenable to therapy would also be identified.

Consequently, there exists a great need for a diagnostic test which will allow physicians to specifically determine whether a cardiac patient is at risk of experiencing a future ischemic event in order that therapy can be employed to prevent or mitigate such subsequent events. The present invention satisfies this need.

SUMMARY OF THE INVENTION

Briefly and in general terms, the present invention provides a new and improved method and means for diagnostically testing cardiac patients and, more particularly, to a diagnostic test which effectively demonstrates a cardiac patient's risk for future ischemic heart events.

In accordance with the present invention, it has been discovered that cardiac patients convalescing from an alerting or "sentinel" ischemic heart event may be evaluated in order to determine whether they are low risk candidates for future ischemic events of the heart. In addition, it has been discovered that these same cardiac patients, upon a determination that they are not low risk, may be evaluated to ascertain the extent of their risk, that is, it can be determined whether these patients are high risk or intermediate risk candidates for future ischemic events of the heart.

Cardiac patients not having a prescribed elevated level of alpha-l-acid glycoprotein (AGP) in their blood plasma and blood serum and not showing a trend of increasing levels of AGP over a selected monitoring period for AGP have been defined as low risk candidates for heart ischemia. Cardiac patients having prescribed elevated levels of AGP who show a trend of increasing levels of AGP over the monitoring period for AGP and who also show an elevated level of CK-MB during the monitoring period for CK-MB have been identified as high risk candidates; elevated levels being defined as an elevated concentration or an elevated activity for CK-MB.

Cardiac patients having an elevated level of AGP, who show a trend of increasing levels of AGP over the monitoring period for AGP and who do not show an elevated level of CK-MB have been identified as intermediate risk candidates.

The levels of AGP and CK-MB in a patient are considered to be elevated when they exceed the respective threshold level for AGP and CK-MB during the monitoring period. The threshold levels for AGP and CK-MB may be defined by two alternative methods. In one method, a particular individual's plasma and serum AGP and CK-MB levels are monitored before any ischemic event occurs to determine normal AGP and CK-MB levels for that individual. The threshold level for AGP would then be the mean AGP level as determined from the monitoring test, increased by the experimental error factor of the test; i.e. increased by a factor determined from the accuracy of and variation in particular monitoring test procedures. The threshold level for CK-MB would be the mean CK-MB level as determined from the monitoring test, increased by the experimental error factor of the test.

In the other method, "normal" individuals are tested to determine normal plasma and serum AGP and CK-MB levels with which comparison can be made. Normal individuals are defined as those age and sex stratified persons with no known disease, the tumor, no cancer, no acute phase reaction, no known infectious disease, no acute inflammation of any organ and without recent known ischemic heart disease. The threshold level for AGP is then defined as the mean plasma and serum AGP levels of normal individuals, increased by two standard deviations. The threshold level for CK-MB under this method is defined as the mean plasma and serum levels of normal individuals, increased by three standard deviations.

The level of AGP in the patient's plasma or serum is monitored in order to determine whether there is an increasing trend. The patients are monitored in this fashion because there are patients with cancer, chronic infection, acute inflammation of an organ, or other such condition who have persistent elevation of AGP above the threshold level for AGP and who are not high or intermediate risk candidates for future ischemic heart events. Consequently, patients who are high or intermediate risk candidates may be distinguished from patients with cancer, chronic infection or acute inflammation of an organ by monitoring the level of AGP over an extended period of time; patients with high or intermediate risk for cardiac events show increasing values during the monitoring period.

One aspect of the present invention is a novel method for assessing whether a cardiac patient is a low risk candidate for future ischemic events of the heart. This method includes monitoring the level of AGP in a cardiac patient's plasma or serum following a sentinel ischemic heart event, comparing the level of AGP in the patient's plasma or serum to the predetermined threshold level for AGP, and determining whether the patient is a low risk candidate for future ischemic heart events. Upon an assessment that the patient is not a low risk candidate, the extent of risk may be subsequently determined by further evaluation.

Consequently, a second aspect of the present invention is a method for assessing whether a cardiac patient is a high, intermediate or low risk candidate for future ischemic events of the heart. This method includes monitoring the level of AGP in a cardiac patient's plasma or serum following an ischemic heart event, monitoring the level of CK-MB in a patient's plasma or serum following an ischemic heart event, comparing the patient's level of AGP to the threshold level for AGP, comparing the patient's level of CK-MB to the threshold level for CK-MB, and determining whether the individual has a high, intermediate or low risk of experiencing recurrent myocardial ischemia.

An additional aspect of the present invention is diagnostic kits which are particularly efficacious in assessing a cardiac patient's risk for future ischemic heart events. One such kit of the present invention comprises a container having therein reagents for an assay for the quantification of AGP and a separate second container having therein reagents for an assay for the quantitification of CK-MB. Another such diagnostic kit of the present invention comprises a container having therein reagents for an assay for the quantification of AGP wherein said reagent is intended to be incubated with plasma or serum containing AGP to assess whether a cardiac patient is a low risk candidate for future ischemic heart events. A third such kit of the present invention comprises a container having therein reagents for an assay for the recognition and quantification of CK-MB wherein said reagent is intended to be incubated with blood plasma or serum containing CK-MB to assess whether a cardiac patient is a high or intermediate risk for future ischemic heart events.

A still further aspect of the present invention is a diagnostic system for assessing a cardiac patient's risk for future ischemic heart events comprising means for measuring the level of AGP in a cardiac patient's plasma or serum and means for measuring the level of CK-MB in a cardiac patient's plasma or serum.

Hence, the present invention satisfies a long existing need in the art for economical, rapid and reliable methods and means for predicting the risk of recurring cardiac ischemic events after the occurrence of a sentinel event. The present invention clearly fulfills this need.

The above and other objects and advantages of the invention will become apparent from the following more detailed description, when taken in conjunction with the accompanying drawing.

BRIEF DESCRIPTION OF THE DRAWING

The single FIGURE of the drawing is a photograph showing the results of a two-dimensional sodium dodecylsulfate gel electrophoresis of AGP.

DETAILED DESCRIPTION

AGP is a glycoprotein having a subunit of molecular weight of about 38,000–46,000 daltons which consists of about 40% carbohydrate. The protein also exists in aggregate forms. The physical properties of AGP of human plasma have been determined by a number of people; a table listing many of these properties is reproduced below:

| PHYSICAL PROPERTIES | VALUES |
|---|---|
| Isoelectric point, | range from 1.8 to 3.8, depending on the technique employed |
| Average electrophoretic mobilities phosphate buffer (I = 0.1), | |
| at pH 2.4 | $+0.72 \times 10^{-5} \text{ cm}^2.\text{v}^{-1}.\text{sec}^{-1}$ |
| at pH 7.6 | $-6.67 \times 10^{-5} \text{ cm}^2.\text{v}^{-1}.\text{sec}^{-1}$ |
| acetate buffer (I = 0.1), | |
| at pH 9.5 | $-3.8 \times 10^{-5} \text{ cm}^2.\text{v}^{-1}.\text{sec}^{-1}$ |
| Average molecular weight | |
| by sedimentation | 44100 |
| | 40000 |
| by sedimentation - diffusion | 41600 |
| by sedimentation - viscosity | 43000 |
| by light-scattering | 40000 |
| by dodecylsulphate polyacrylamide gel electrophoresis | 40000 |
| | 40000 and 80,000 depending on buffer |
| Coeffecient of friction, $\frac{f}{f_o}$ | 1.78 |
| Viscosity increment, V | 10.2 |
| Optical rotation, $[\alpha]_D^{25}$ | |
| at pH 3.4 | $-53.1°$ |
| at pH 5.8 | $-28.8°$ |
| at pH 9.4 | $-21.1°$ |
| Absorption Value, $E^{1 \text{ cm}}$ at 278 nm 1% | 8.93 |
| Refractive index increment, $\Delta_n/\Delta_K$ | $1.80 \times 10^{-4}$ |

Referring now to the drawing, there is shown a high resolution two-dimensional gel electrophoretogram of alpha-l-acid glycoprotein derived from normal human serum. The method used was described by Anderson, L. and Anderson N. G., Proc. Natl. Acad. Sci. USA, 74: 5421–5425, 1977. The pH values for isoelectric focusings ranged from pH 3.5 to pH 5. Because urea is included in the method, only apparent pH values were obtained. True pH values are considerably more acidic. Isoelectric focusing was in the horizontal direction, with the most acidic end on the left side of the gel. The second dimension is a sodium dodecylsulfate gel electrophoresis, where the smaller molecular weight compounds migrate the fastest. The fastest migrating subgroup, with a more basic pH value, had a molecular weight of 38,000 daltons and an apparent pH of 4.6. The most acidic component, with an apparent pH of 4.1, had a molecular weight of 46,000 daltons.

The arrows in the drawing indicate the resolution of normal AGP serum according to the isoelectric point and the molecular weight. All other areas, not similarly identified by arrows, represent artifacts or other material irrelevent to the identification of the AGP molecule.

The complete amino acid sequence for AGP has been determined. Considerable variations in the sequence have been observed in several positions. The sites of glycosylation have been identified and structures for the carbohydrate containing side chains have been obtained. Considerable heterogeneity can exist due to variations in glycosylation and due to amino acid sequence changes. High resolution two-dimension gel electrophoresis readily resolves acid glycoproteins into as many as 6–10 subgroups. Therefore, the term AGP, as used herein, refers to all forms, components and subunits of AGP which are correlative in the ischemic event prediction process.

Several methods are available to measure the level of AGP in plasma or serum including immunoassays such as nephelometric, immunofluorescent assays, ELISA, radioimmunoassays, immunodiffusion, rocket immunoassays, electrophoretic separations or other suitable methods. There are also several methods available to measure the level of CK-MB in plasma or serum including electrophoretic separation, ion exchange chromatography, immunoinhibition and other appropriate techniques. Those skilled in the art will readily appreciate those methods which can be used to determine the level of either AGP or CK-MB.

One technique for determining the level of AGP in plasma or serum is carried out as a liquid phase radioimmunoassay which may be performed as follows. The plasma or serum is incubated together with the radioisotopically (preferably $^{125}I$) labeled AGP and antibody recognizing AGP in a buffer comprised of usual components useful in radioimmunoassays. A significant period of time is allowed to achieve appropriate binding of the AGP and antibody. After incubation, the labeled and unlabeled AGP is separated from the free labeled and unlabeled AGP by standard methods such as treatment with polyethylene glycol or reaction with a second antibody. The second antibody should be specified for the immunoglobulins of the host species in which the first antibody was raised. Such second antibody preparations are obtained by standard techniques. The radioactivity from either the bound or the free material is measured and the concentration of AGP present in the sample is determined through reference to a standard curve. The standard curve is derived by incubating fixed amounts of $^{125}I$ AGP in the presence of a known concentration of antisera, with various known concentrations of AGP, and plotting the amount of radioactivity observed against the known concentrations of AGP.

Another method to measure the concentration of AGP in plasma or serum is an enzyme-linked-immunosorbent-assay (ELISA). In this assay, the antibody in the antiserum against the AGP is purified and adhered to a solid support, such as nylon film, nylon beads, sepharose beads, glass film, glass beads, polystyrene or other appropriate form of solid support, to form an immunosorbent. The plasma or serum is then incubated with the immunosorbent to form an AGP immunosorbent complex. The AGP immunosorbent complex is then separated from the remaining plasma or serum constituents and reacted with a second antibody against the AGP to form a "sandwich".

The presence of second antibody on the AGP immunosorbent complex is detected by one of several methods. One method is to bind an enzyme marker to a second antibody such as alkaline phosphatase. The sandwhich is then exposed to the substrate of alkaline phosphatase and a color is produced by the enzyme activity. There is a direct linear relationship between the amount of AGP bound and the production of color by the alkaline phosphatase reaction. With the appropriate use of known standards for the AGP, the amount of unknown AGP from the body fluid can be detected. Alternatively, many different enzymes such as glucose oxidase, horseradish peroxidase and others may be used as the marker. A second method to detect the sandwich would be to use a third antibody against the second antibody, to form a double sandwich. This third antibody would then be connected to a marker enzyme, for example, alkaline phosphatase. The double sandwich would then be detected in a similar manner by the development of color. The marker enzyme could be detected colorimetrically or fluorometrically. Finally, instead of the marker enzyme, the sandwich could be detected by use of a radioactive label, a fluorescent label, or any other appropriate label.

The antibody to the immunogen AGP is prepared by any of several methods. For instance, hybridoma technology may be used to produce monoclonal antibodies that will specifically react with AGP. The antibody may also be prepared by injecting the AGP into a host animal, preferably accompanied by an adjuvant. An example of a suitable adjuvant is Freund's complete adjuvant, an agent which enhances the inflammation response. Improved antibody titres can be obtained by repeated injections over a period of time infrequently accompanied by an agent which nonspecifically enhances the immunological response, such as pertussis vaccine. Suitable host animals for this purpose include mammals such as rabbits, horses, goats, guinea pigs, rats, mice, cows, and sheep. The resulting antisera will contain antibodies which will recognize and bind to AGP. The antisera can be further purified by immunoglobulin precipitation and affinity purification. Affinity purification requires the bonding of purified AGP to a solid phase support, passing the antisera or other immunoglobulin fraction over the affinity column, and subsequently eluting the specific AGP antibodies. The affinity purified antibodies are useful for all immunoassays.

The source of immunogen AGP to prepare antisera or monoclonal antibodies against AGP may be any organ or physiological fluid which has significant levels of AGP. Examples of such organs are heart, brain, liver and spleen. The plasma of patients convalescing from a myocardial infarction also constitutes a suitable source of immunogen AGP.

There are several methods to measure the level of CK-MB in plasma and serum. The ion exchange chromatographic separation method, from which the data included in this application has been generated, is well known in the art and has been described by Shell et al, Sensitivity and Specificity of MB-Creatine Kinase Activity Determined with Column Chromatography, Am. J. Cardiol., 44: 67, 1979. Other assay systems which could be used include electrophoretic, other ion exchange methods, immunoinhibition and other immunologic methods.

In accordance with the present invention, the level of AGP and CK-MB are monitored for a period of time after the sentinel event. For a single sentinel event, it will require approximately 12–24 hours following the initiation of the event for the AGP level to begin increasing. It will continue to increase for approximately one to four days following the initiation of the event. Also, the increased level of AGP will remain in the plasma and serum for a prolonged period; AGP has a half life of approximately 21 days. Consequently, in order to determine whether there is a trend of increasing levels of AGP, its level is monitored during the one to four day period following the initiation of the sentinel event. A trend of increasing levels of AGP combined with an elevated level of AGP during the monitoring period indicates that the patient is not a low risk candidate.

In order to determine the extent of risk of a patient who shows a trend of increasing levels of AGP and an elevated level of AGP during the monitoring period, the level of CK-MB is monitored after the sentinel event. Unlike AGP, the level of CK-MB will begin to increase rather rapidly (if at all) after the initiation of the sentinel event. In addition, the level of CK-MB will increase for a shorter period of time than will AGP. Consequently, the level of CK-MB is preferably monitored for the two days following the sentinel event. An elevated level of CK-MB during the monitoring period for CK-MB combined with an elevated level and a trend of increasing levels for AGP is indicative of a high risk candidate. An unelevated level of CK-MB during the monitoring period for CK-MB combined with an elevated level and a trend of increasing levels for AGP is indicative of an intermediate risk candidate.

The high, intermediate and low risk candidates for recurrent heart ischemia can be defined in terms of clinical syndromes. Ischemia refers to tissue damage which results from a reduced blood flow falling below the metabolic needs of an organ. Heart ischemia, then, is damage to the heart tissue resulting from an inadequate supply of blood which overburdens that organ. The recognized heart ischemic syndromes include myocardial infarction, unstable angina pectoris, and sudden cardiac death. Myocardial infarction is defined as necrosis of the heart associated with an increase of CK and CK-MB in the serum, and well defined electrocardiographic changes. Unstable angina pectoris is chest pain, consistent with ischemic heart disease, characterized by changing electrocardiographic signs without an increase in the known conventional enzyme tests for total CK, CK-MB, SGOT, and LDH activities. Sudden cardiac death is a syndrome associated with death occurring within 24 hours of an alteration of patient symptoms. The death occurs without known trauma or other known disease, and can occur in patients with or without known ischemic heart disease. The literature indicates that the majority of such deaths are associated with coronary atherosclerotic heart disease.

High risk for recurrent ischemic heart disease is defined as a cohort of patients with an increased probability of a recurrent ischemic event—myocardial infarction, unstable angina, sudden cardiac death—when compared to a normal population and a population of general admissions to a coronary care unit (CCU). The low risk cohort is defined as patients with a reduced risk of recurrent ischemic events compared to both a normal population and to a general CCU population. The intermediate risk cohort lies between the high and low risk cohorts. This invention enables the high, intermediate and low risk cohorts to be identified. The cohorts are identified by the invention shortly after the sentinel ischemic event such that prognosis for up to 12 months can be determined.

For purposes of the discussion of the invention, high risk is defined as a mortality of greater than 25% within 6 months of the sentinel event, intermediate risk as 1–25% in 6 months, and low risk as less than 1%. This classification allows homogeneous subsetting of what heretofore has been a heterogeneous cohort.

The following examples will serve to illustrate the present invention in accordance with a preferred embodiment.

EXAMPLE 1

PREPARATION OF AGP

Human brain tissue was obtained at autopsy within twenty-four hours post mortem, preferably within hours of death. The tissue was cleared of fat and durameter, divided into approximate 100 g quantities, and stored at $-20°$ until use. A 100 g quantity of brain tissue was thawed, cut into small pieces with scissors, and homogenized in a precooled ($4°$ C.) Waring blender in 2 ml/g of 50 mmol/L Tris-HCl, pH 7.4 containing 5 mmol/L 2-mercaptoethanol for three bursts of 15 seconds each. The homogenate was centrifuged at $20,000 \times g$ for 20 minutes and the supernatant fraction saved. This and all subsequent purification steps were carried out at $0°-4°$ C.

The centrifuged homogenate was brought to a concentration of 60% ethanol by dropwise addition of 1.72 volumes of 95% ethanol, that had been prechilled to $-20°$ C., to the stirred extract. After stirring for 30 minutes, the precipitated protein was removed by centrifugation for fifteen minutes, at $2,100 \times g$, and the supernatant fraction was brought to a concentration of 78% ethanol by the dropwise addition of a volume of prechilled 95% ethanol equal to 2.86 times the volume of the centrifuged homogenate. After stirring for 30 minutes, the 60–78% ethanol precipate was collected by centrifugation for 15 minutes at $2,100 \times g$, and redissolved with a Douce homogenizer into 15 ml at 50 mmol/L Tris-HCl, ph 7.4 containing 100 mmol/L NaCl and 5 mmol/L 2-mercaptoethanol. Protein that could not be redissolved was removed by centrifugation for 20 minutes at $50,000 \times g$.

The 60–78% ethanol fraction was applied to a $2.5 \times 25$ cc column of DEAE A-50 Sephadex that had previously been equilibrated and washed several times with 50 mmol/L Tris-HCl, pH 7.5 containing 100 mmol/L 2-mercaptoethanol. Eluate fractions were examined spectrophotometrically at 280 nm for protein content and approximately pooled.

The glycoprotein containing pool from the DEAE-Sephadex column was brought to a 2% perchloric acid concentration by the slow addition of 0.0345 volumes of 60% perchloric acid while stirring. After 30 minutes, the precipitated material was removed by centrifugation for 30 minutes at $8000 \times g$. The supernatant fraction was dialyzed three times against 50 volumes of 50 mmol/L Tris-HCl, ph 7.4 and concentrated by ultrafiltration using an Amicon CF25 membrane cone. The glycoprotein preparation was frozen for long-term storage.

EXAMPLE 2

Production of antisera against AGP

Two adult New Zealand white rabbits were immunized against AGP. The rabbits were injected intramuscularly at multiple sites of the thigh with a total of 500 ug of protein emulsified in complete Freund's adjuvant for the primary immunization, then subsequently with a 50 ug of protein emulsified in incomplete Freund's adjuvant. The rabbits are bled 10-14 days after each injection and the immunological response monitored by immunoelectrophoresis. All antisera were divided into aliquots and stored at −20° C.

EXAMPLE 3

Radioiodination of Glycoprotein

The simple method using Iodogen (1, 3, 4, 6 tetrachlora−3α, 6α—diphenylglycouril) as the iodinating reagent proved to be a gentle, effective technique for the labeling of a glycoprotein with $^{125}$I. The method was as follows: a solution of Iodogen (100 ul:1 mg-ml) dissolved in chloroform was allowed to dry under $N_2$ gas at the bottom of a 10×75 mm borosilicate glass tube. 50 ug of glycoprotein dissolved in 200 ul of 0.10M phosphate buffer pH 7.4 was added to the coated tube. The iodination reaction was initiated with the addition of 1 mCi $^{125}$I in 10 ul. After 10 minutes with occasional gentle mixing, the reaction was terminated by transferring the iodination mixture with a Pasteur pipet to a Bio-Gel P60 column (20×0.6 cm) equilibrated in phosphate buffer saline (PBS), pH 7.4. Chromatography was carried out to separate the labeled protein from $^{125}$I with 0.5 ml fractions collected into 0.5 ml of 0.1% Tween 20-PBS, pH 7.4. The final specific activity assumes total recovery of glycoprotein from the column and homogenous labeling of the protein.

EXAMPLE 4

Radioimmunoassay for Acid Glycoprotein

The procedure performed to assay for plasma AGP is as follows:

| ADD: | AGP standard/plasma sample (1/250 dilution) | 25 ul |
| --- | --- | --- |
| | $^{125}$I - labeled AGP | 100 ul |
| | anti-AGP rabbit serum (First antibody) | 100 ul |
| INCUBATE: | 60 min at 37° C. | |
| ADD: | Goat anti-rabbit immunoglobulin serum (Second antibody) | 100 ul |
| INCUBATE: | 30 min. at room temperature | |
| ADD: | 5% polyethylene glycol in water (Wall Wash) | 500 ul |
| CENTRIFUGE: | 15 min. at 4° C., 3000 × g | |
| ASPIRATE: | Supernatant (discard) | |
| COUNT: | Radioactivity of the pellet for 1 min. | |

All determinations were done in triplicate in 12×75 mm borosilicate glass tubes. All reagent dilutions were made in PBS as described. In the assay all plasma samples were run in an identical manner as the standard. Each tube contained 100,000–150,000 CPM of iodinated AGP which averaged about 20 ng of protein. A dilution of anti-AGP rabbit serum in 1% normal rabbit serum producing 70% binding of labeled AGP was chosen as the first antibody. Following incubation, a dilution of goat anti-serum to rabbit serum was added to all the tubes to separate the free from bound antigen by the second antibody technique. Following incubation a wall wash was added to all the tubes, they were then centrifuged, supernatant aspirated and the radioactivity of the pellet was determined for one minute.

EXAMPLE 5

ELISA for AGP

Sample dilutions were placed in 2% Bovine serum albumin (BSA) in 0.015M Phosphate buffer, pH 7.2, containing 0.15M NaCl and 0.02% Tween—20 (PBS-Tween). The tests were performed in 12×75 mm borosilicate glass tubes, 1 bead/test. The nylon beads were activated by a brief treatment with glutaraldehyde, and extensive washing. As a result, the affinity purified immunoglobulins to AGP were adsorbed to the bead surfaces.

Procedure

1. Half ml aliquots of blanks, standard AGP dilutions and samples, all in triplicate, were added to beads and incubated for 2 hours at 37° C. in a shaker bath at 100 rpm.

2. The liquid was aspirated and each bead was washed three times with 1 ml of PBS-Tween for 10 minutes at 37° C. at 100 rpm.

3. A half ml aliquot of suitably diluted conjugate of AGP-antibody with alkaline phosphatase was added to each bead and incubated at 100 rpm for one hour at 37° C.

4. The liquid was aspirated and each bead was washed once with 1 ml of PBS-Tween and then two times with 1 ml of PBS for 10 minutes at 37° C. at 100 rpm.

5. Each bead was transferred to 1 ml of NPP reagent (1 mg para-nitrophenyl phosphate (NPP) per ml in 0.5M carbonate buffer pH 9.8 containing 1 mM $MgCl_2$) and incubated for 30–60 minutes at 37° C. at 100 rpm.

6. The reaction was stopped with 0.1 ml of 2N NaOH. The optical densities (O.D.) read at 405 nm against an NPP reagent blank.

7. The standard curve was constructed by subtracting the bead blank and plotting the standard concentration against the log of its O.D.

EXAMPLE 6

Detection of CK-MB may be performed by ion exchange chromatography as described earlier in Shell et al, Sensitivity and Specificity of MB-Creatine Kinase Activity Determined with Column Chromatography, Am. J. Cardiol. 44:67, 1979.

EXAMPLE 7

Determination of the threshold levels for AGP and CK-MB

Normal subjects: A cohort of normal subjects (n=49) were analyzed to assess the normal range for AGP. The normal value was obtained by using the radioimmunoassay of Example 4. Normal individuals were defined as those who claimed to be normal and in whom there was no known history of ischemic heart disease, tumor, cancer, or other chronic inflammatory disease as determined by examination. Individuals were excluded if they had known acute inflammation including infectious disease, acute trauma or chronic infectious disease. This population included a range of age and sex distribution. The normal concentration for AGP was 249 ug/ml and the standard deviation was 53 ug/ml (n=49). It should be pointed out that the concentration of AGP measured by this assay is less than other assays. For example, immunodiffusion and nephelometry determinations claim a normal value of about 900-1000 ug/ml.

Thus, the threshold for AGP must be established for each assay system used to determine risk.

The threshold value for plasma and serum AGP concentrations was defined as 355 ug/ml (mean+two standard deviations).

The threshold value for CK-MB activity was 5.1 Iu/L (mean+3 standard deviations) using ion exchange chromatography. As for AGP, the value for the threshold must be established for each assay system for CK-MB.

EXAMPLE 8

Long term follow-up

A small cohort (cohort I), admitted to a coronary care unit in order to rule out a myocardial infarction, was prospectively studied for one year (n=31). The patients were included if they had ischemic chest pain, ST-segment depression on their initial ECG and no initial new o-waves. The patients underwent blood sampling every four hours for 24 hours.

The patients were then followed for one year after hospital discharge and new ischemic events assessed. The new ischemic events were designated as either: (1) a new transmural acute myocardial infarction, (2) a new nontransmural acute myocardial infarction, or (3) a sudden death. A new transmural acute myocardial infarction was defined as a new chest pain episode with development of o-waves. A new non-transmural acute myocardial infarction was defined as ischemic chest pain initiating a second hospitalization associated with ST-segment depression and evolution of CK-MB activity. Sudden death was defined as death within 24 hours of new unexpected symptoms. There was 100% follow-up. The demographics for the group are in Table I.

The threshold values for AGP and CK-MB used to determine whether the levels of AGP and CK-MB were elevated were those reported in Example 7. There were 22 new ischemic events in the 19 patients with elevated AGP, including 5 sudden deaths. There were no new ischemic events and no deaths in the patients with normal AGP concentration. Of the 19 patients with elevated AGP, 12 experienced at least one new ischemic event compared to none in the 12 with normal AGP. In the 31 patients, 11 had elevated CK-MB, including 3 who experienced sudden death. There were two deaths in the patients who had normal CK-MB activity. All 11 patients with elevated CK-MB activity had at least one new ischemic event while 4 of 20 with normal CK-MB activity had new ischemic events. The results are tabulated in Table II.

The 31 patients were then classified into three groups: (1) elevated AGP and elevated CK-MB, (2) elevated AGP alone, and (3) normal AGP. The incidence of new ischemic events in 12 months was 100% in Group 1, 33% in Group II and 0% in Group III. The mortality rate was 37.5% (3 of 8) in Group 1, 18% (2 of 11) in Group II and 0% in Group III (0 of 12). The results are tabulated in Table III.

TABLE I

| Patient Demographics (cohort I) | |
|---|---|
| Number = 31 | Age = 65. +/− 13.8 |
| Male/Female = 22/9 | Chest Pain on Admission = 100% |
| ST Depression = 100% | One Year Mortality = 16% |
| | In-hospital Mortality = 0% |

TABLE II (cohort I)
Incidence of New Ischemic Events in Patients with Chest Pain

| | No. of Patients | No. of Ischemic Events | No. of Pts. with new Ischemic Events | No. of Sudden Deaths |
|---|---|---|---|---|
| AGP Elev. | 19 | 22 | 12 | 5 |
| AGP NML | 12 | 0 | 0 | 0 |
| CK-MB Elev. | 11 | 16 | 11 | 3 |
| CK-MB NML | 20 | 6 | 4 | 2 |

TABLE III

Incidence of Ischemic Events in Patients with Chest Pain (cohort I)

| AGP | CK-MB | No. of Patients | No. of Pts. with new Ischemic Events | No. of Sudden Deaths |
|---|---|---|---|---|
| Elev. | Elev. | 8 | 8 | 3 |
| Elev. | Nml | 11 | 4 | 2 |
| Nml | | 12 | 0 | 0 |

EXAMPLE 9

Short Term Followup

Because of the observations in Example 8, we selected 146 consecutive patients admitted to our CCU to evaluate potential ischemic syndromes. The admissions were to identify or rule out myocaridal infarction. Not considered for selection were patients with initial ST-segment elevation because their prognoses are known. Additionally, patients with neither ischemic symptoms (chest pain) or ischemia on their ECG were excluded.

After twenty-four hours of observation, one of three diagnostic classes were applied based on electrocardiographic and enzymatic findings:
  A. Transmural acute myocardial infarction (n=35): evolution of new o-waves within 24 hours of admission. These patients have elevated AGP when sequentially sampled.
  B. Nontransmural acute myocardial infarction, AMI (n=19); ischemic chest pain, sustained ST-segment depression and an elevation in CK-MB activity to more than 15 IU/L (normal values are less than or equal to 5.1 IU/L) in the 24 hour period following admission. The choice of 15 IU/L was somewhat arbitrary but is based on previous observations that a CK-MB activity of less than 15 IU/L corresponded to an infarct of less than 1 CPK-gm-equivalent. Shell et al, Sensitivity and Specificity of MB-Creatine Kinase Activity with Column Chromatography, Am. J. Cardiol., 44:67, 1979, and Roberts et al, An Improved Basis for Enzymatic Estimation of Infarct Size, Circulation 52:743 1975.
  C. Ischemic chest pain without acute myocardial infarction (n=92): ischemic chest pain, nonspecific ST-segment changes on their ECG, no o-waves in the 24 hour period following admission and a CK-MB activity of less than 15 IU/L.

The AGP, when sampled serially, was elevated in all 35 patients with transmural AMI. The average value of highest observed readings for each patient was approximately 400 ug/ml. In transmural AMI, the AGP began to increase at the peak of CK-MB activity, reached a peak value at 48 hours, and remained elevated for upwards of 8 days.

The demographic pattern of the 111 patients (B and C above) (cohort 2) who did not develop a transmural acute myocardial infarction during the observation period is presented in Table IV.

Of the 111 patients who did not develop a transmural acute myocardial infarction, there were 32/111 (29%) patients with normal AGP; 35/111 (32%) with elevated AGP only and 44/111 (40%) with elevated AGP and elevated CK-MB. Of the 44 patients with elevated AGP and elevated CK-MB, 26 (59%) had CK-MB values between 5 and 15 IU/L—a range considered "minimal" elevation by many.

The one and six month mortality rates were correlated to the presence of AGP in plasma. In the 44 patients with elevated CK-MB and elevated AGP, there were 14 deaths (32%) by one month. By six months, an additional two deaths had occurred in this group bringing the total mortality to 36% (16/44). In the 35 patients with elevated AGP alone, there were 5 deaths (14%) by one month, with an additional 2 deaths occurring by six months for a total six month mortality rate of 20% (7/35). In the 32 patients with normal AGP there were no deaths. The results are tabulated in Table V.

When the patients were classified by AGP alone, 19 of 79 who had elevated AGP died within one month (24%) compared to none of the normal AGP negative group. By six months, the mortality rate for those with elevated AGP was 29% (23/79) compared to no deaths in the normal AGP group. When the 111 patients were classified by their CK-MB activities, the 6 month mortality rate for the group was elevated CK-MB was 36% (16/44). The mortality rate for the CK-MB normal patients was 10% (7/67).

To assess the relationship between the biochemical classification and the clinical signs, the Killip-Scheidt clinical classification was determined for each patient and subsequently compared to the AGP and CK-MB levels. In patients with elevated AGP and CK-MB, 57% (25/44) were Killip-Scheidt Class 1. Of the patients with normal AGP and CK-MB, 88% (28/32) were Killip-Scheidt Class 1.

Since the mortality rates were higher than initially anticipated, the characteristics of individual patients were examined. The characteristics analyzed in order to obtain a complete clinical definition of status and cause of death were initial clinical status, Killip-Scheidt classification and the initial symptoms which include pain and shortness of breath. The characteristics of patients who died and who had elevated CK-MB and AGP are listed in Table VI. The characteristics of the patients who did not have elevated AGP were indistinguishable from the patients with elevated AGP.

TABLE IV

Demographics for Cohort 2

Number = 111  Age = 69.9 +/− 12.6
Male/Female = 57/54  Chest Pain on Admission = 77%
ST Depression = 100%  Six Month Mortality = 16%
  In-hospital Mortality = 13%

TABLE V

Relationship of AGP and CK-MB Activity to 1 and 6 month mortality

| AGP | CK-MB | No. of Patients | 1 Mo. Mortality Rate | 6 Mo. Mortality Rate |
|---|---|---|---|---|
| Elev. | Elev. | 44 | 32% (14/44) | 36% (16/44) |
| Elev. | Nml. | 35 | 14% (5/35) | 20% (7/35) |
| Nml. |  | 32 | 0% (0/32) | 0% (0/32) |
| Elev. |  | 79 | 24% (19/79) | 29% (23/79) |
| Nml. |  | 32 | 0% (0/32) | 0% (0/32) |
|  | Elev. | 44 | 33% (14/44) | 36% (16/44) |
|  | Nml. | 67 | 9% (6/67) | 10% (7/67) |

TABLE VI

Relationship of Enzyme Level to Killip Class

| AGP | CK-MB | No. of Pat. | % K1 | % K2-3 | % with Pain as Initial Symptoms | % with Shortness of Breath as Initial Symptoms |
|---|---|---|---|---|---|---|
| Elev | Elev. | 44 | 57 | 43 | 68 | 32 |
| Elev. | Nml. | 35 | 77 | 23 | 91 | 6* |
| Nml. |  | 32 | 88 | 13 | 91 | 9 |

*1 Patient with syncopy

The aforedescribed methods and means satisfy a long existing need in the medical arts for economical, rapid and reliable assessment and prediction of the risk of recurring cardiac ischemic events after the occurrence of an alerting sentinel event in a cardiac patient.

While various forms of the invention have been disclosed, it will be appreciated that modifications may be made herein without departing from the spirit and scope of the invention. Accordingly, the invention is not to be limited, except as by the appended claims.

We claim:

1. A method for assessing a cardiac patient's risk for future ischemic heart events comprising the steps of:
   (a) monitoring the level of alpha-1-acid glycoprotein in a cardiac patient's plasma or serum following an ischemic heart event;
   (b) comparing the levels of alpha-1-acid glycoprotein measured in step (a) to a threshold level for alpha-1-acid glycoprotein; and
   (c) determining whether said cardiac patient has a low risk of experiencing future ischemic heart events.

2. A method for assessing a cardiac patient's risk for future ischemic heart events comprising the steps of:
   (a) monitoring the level of alpha-1-acid glycoprotein in a cardiac patient's plasma or serum following an ischemic heart event, for a prescribed period of time for alpha-1-acid glycoprotein;
   (b) comparing the levels of alpha-1-acid glycoprotein measured in step (a) to a prescribed threshold level for alpha-1-acid glycoprotein; and
   (c) determining whether said patient has a low risk of experiencing future ischemic heart events based upon the trend of alpha-1-acid glycoprotein levels monitored in step (a) and the comparison of step (b).

3. A method as set forth in claim 2, wherein said prescribed period of time for alpha-1-acid glycoprotein is about 1 to about 4 days following the ischemic event.

4. A method as set forth in claim 2, wherein said prescribed threshold level is the mean level of alpha-1- acid glycoprotein in normal individuals increased by two standard deviations.

5. A method for assessing a cardiac patient's risk for future ischemic heart events comprising the steps of:
   (a) monitoring the level of alpha-1-acid glycoprotein in a cardiac patient's plasma or serum following an ischemic heart event for a prescribed period of time for alpha-1-acid glycoprotein;
   (b) determining a threshold level for alpha-1-acid glycoprotein from a suitable sized population of normal individuals;
   (c) comparing the levels of alpha-1-acid glycoprotein measured in step (a) to the threshold level determined in step (b); and
   (d) determining whether said patient has a low risk of experiencing future ischemic heart events based upon the trend of alpha-1-acid glycoprotein levels monitored in step (a) and the comparison of step (c).

6. A method for assessing a cardiac patient's risk for future ischemic heart events comprising the steps of:
   (a) monitoring the level of alpha-1-acid glycoprotein in a cardiac patient's plasma or serum following an ischemic heart event for a prescribed period of time for alpha-1-acid glycoprotein;
   (b) determining a threshold level for alpha-1-acid glycoprotein for said patient by monitoring the level of alpha-1-acid glycoprotein in said patient's serum or plasma over a period of time prior to an ischemic event;
   (c) comparing the levels of alpha-1-acid glycoprotein measured in step (a) to the threshold level determined in step (b); and
   (d) determining whether said patient has a low risk of experiencing future ischemic heart events based upon the trend of alpha-1-acid glycoprotein levels monitored in step (a) and the comparison of step (c).

7. A method for assessing a cardiac patient's risk for future ischemic heart events comprising the steps of:
   (a) monitoring the level of alpha-1-acid glycoprotein in a cardiac patient's plasma or serum following an ischemic heart event;
   (b) monitoring the level of CK-MB in a cardiac patient's plasma or serum following said ischemic heart event;
   (c) comparing the levels of alpha-1-acid glycoprotein measured in step (a) to a threshold level for alpha-1-acid glycoprotein;
   (d) comparing the levels of CK-MB measured in step (b) to a threshold level for CK-MB; and
   (e) determining whether said cardiac patient is a high, intermediate or low risk candidate for future ischemic heart events.

8. A method for assessing a cardiac patient's risk for future ischemic heart events comprising the steps of:
   (a) monitoring the level of alpha-1-acid glycoprotein in a cardiac patient's plasma or serum following an ischemic heart event, for a prescribed period of time for alpha-1-acid glycoprotein;
   (b) monitoring the level of CK-MB in said cardiac patient's plasma or serum following said ischemic event for a prescribed period of time for CK-MB;
   (c) comparing the levels of alpha-1-acid glycoprotein measured in step (a) to a prescribed threshold level for alpha-1-acid glycoprotein; and
   (d) comparing the levels of CK-MB measured in step (b) to a prescribed threshold level for CK-MB;
   (e) determining that said patient is a high risk candidate for future ischemic events if the level of CK-MB is elevated as determined by step (d), the level of alpha-1-acid glycoprotein is elevated as determined by step (c) and the level of alpha-1-acid glycoprotein demonstrates an increasing trend determined from step (a); and
   (f) determining that said patient is an intermediate disk candidate for future ischemic events if the level of CK-MB is not elevated as determined by step (d), the level of alpha-1-acid glycoprotein is elevated as determined by step (c) and the level of alpha-1-acid glycoprotein demonstrates an increasing trend determined from step (a).

9. A method as set forth in claim 8, wherein said prescribed period of time for alpha-1-acid glycoprotein is about 1 to about 4 days following said ischemic event and wherein said prescribed period of time for CK-MB is about 2 days following said ischemic event.

10. A method as set forth in claim 8, wherein said prescribed threshold level for alpha-1-acid glycoprotein is the mean level of alpha-1-acid glycoprotein in normal individuals increased by two standard deviations.

11. A method as set forth in claim 8, wherein said prescribed threshold level for CK-MB is the mean level of CK-MB in normal individuals increased by three standard deviations.

12. A method for assessing a cardiac patient's risk for future ischemic events comprising the steps of:
   (a) monitoring the level of alpha-1-acid glycoprotein in a cardiac patient's plasma or serum following an ischemic heart event for a prescribed period of time for alpha-1-acid glycoprotein;
   (b) monitoring the level of CK-MB in said cardiac patient's plasma or serum following said ischemic event for a prescribed period of time of CK-MB;
   (c) determining a threshold level for alpha-1-acid glycoprotein;
   (d) determining a threshold level for CK-MB;
   (e) comparing the levels of alpha-1-acid glycoprotein measured in step (a) to the threshold level determined in step (c);
   (f) comparing the levels of CK-MB measured in step (b) to the threshold level determined in step (d);
   (g) determining that said patient is a high risk candidate for future ischemic events if the level of CK-MB is elevated as determined in step (f), the level of alpha-1-acid glycoprotein is elevated as determined by step (e) and the level of alpha-1-acid glycoprotein demonstrates an increasing trend as determined by step (a); and
   (h) determining that said patient is an intermediate risk candidate for future ischemic events if the level of CK-MB is not elevated as determined by step (f), the level of alpha-1-acid glycoprotein is elevated as determined by step (e) and the level of alpha-1-acid glycoprotein demonstrates an increasing trend as determined by step (a).

13. A method as set forth in claim 12, wherein said threshold level for alpha-1-acid glycoprotein is determined from a suitable sized population of normal individuals.

14. A method as set forth in claim 12, wherein said threshold level for CK-MB is determined from a suitable sized population of normal individuals.

15. A method as set forth in claim 12, wherein said threshold level for alpha-1-acid glycoprotein is determined by monitoring the level of alpha-1-acid glycoprotein in said patient's serum or plasma over a period of time prior to an ischemic event.

16. A method as set forth in claim 12, wherein said threshold level for CK-MB is determined by monitoring the level of CK-MB in said patient's serum or plasma over a period of time prior to an ischemic event.

* * * * *

UNITED STATES PATENT AND TRADEMARK OFFICE
CERTIFICATE OF CORRECTION

PATENT NO. : 4,492,753                                      Page 1 of 3

DATED      : January 8, 1985

INVENTOR(S) : William E. Shell, Michael H. Burnam, Zoltan A. Tokes

It is certified that error appears in the above—identified patent and that said Letters Patent is hereby corrected as shown below:

In Column 2, line 53, delete "the" and insert therefor -- no --.

In Column 5, line 42, delete "specified" and insert therefor -- specific --.

In Column 8, line 16, delete "cleared" and insert therefor -- cleaned --.

In Column 8, line 17, after "-20°" add -- C. --.

In Column 9, line 3, delete "are" and insert therefor -- were --.

In Column 11, line 20, delete "o-waves" and insert therefor -- Q-waves --.

In Column 11, line 29, delete "o-waves" and insert therefor -- Q-waves --.

UNITED STATES PATENT AND TRADEMARK OFFICE
CERTIFICATE OF CORRECTION

PATENT NO. : 4,492,753

DATED : January 8, 1985

INVENTOR(S) : William E. Shell, Michael H. Burnam, Zoltan A. Tokes

It is certified that error appears in the above-identified patent and that said Letters Patent is hereby corrected as shown below:

In Column 11, line 64, delete "65." and insert therefor --65.1--.

In Column 12, line 32, delete "myocaridal" and insert therefor --myocardial--.

In Column 12, line 38, delete "were" and insert --was--.

In Column 12, line 42, delete "o-waves" and insert therefor --Q-waves--.

In Column 12, line 47, after "(n=19)" delete ";" and insert therefor --:--.

In Column 12, line 61, delete "o-waves" and insert therefor --Q-waves--.

In Column 13, line 36, delete "was" and insert therefor --with--.

UNITED STATES PATENT AND TRADEMARK OFFICE
CERTIFICATE OF CORRECTION

PATENT NO. : 4,492,753                  Page 3 of 3

DATED : January 8, 1985

INVENTOR(S) : William E. Shell, Michael H. Burnam, Zoltan A. Tokes

It is certified that error appears in the above-identified patent and that said Letters Patent is hereby corrected as shown below:

In Column 16, line 5, delete "disk" and insert therefor --risk--.

In column 16, line 31, delete "of", second occurence, and insert therefor -- for--.

Signed and Sealed this

*Fifteenth* Day of *October 1985*

[SEAL]

*Attest:*

DONALD J. QUIGG

*Attesting Officer*        *Commissioner of Patents and Trademarks—Designate*